United States Patent [19]

Kenny

[11] Patent Number: 4,735,092
[45] Date of Patent: Apr. 5, 1988

[54] APPARATUS FOR RUPTURE TESTING METAL FILMS

[75] Inventor: James Kenny, Baldwinsville, N.Y.

[73] Assignee: EMK Testing Company, Inc., Cicero, N.Y.

[21] Appl. No.: 938,596

[22] Filed: Dec. 5, 1986

[51] Int. Cl.$^4$ .............................................. G01N 3/00
[52] U.S. Cl. ...................................................... 73/840
[58] Field of Search ................. 73/838, 840, 816, 839, 73/159

[56] References Cited

U.S. PATENT DOCUMENTS

| 1,496,838 | 6/1924 | Batcheller | 73/839 |
| 1,605,311 | 11/1926 | Webb | 73/840 |
| 2,332,818 | 10/1943 | Smith | 73/840 |
| 2,748,596 | 6/1956 | Tasker | 73/838 |
| 3,050,991 | 8/1962 | Madrzyk et al. | 73/840 |
| 3,477,287 | 11/1969 | Dubach | 73/838 |
| 3,993,479 | 11/1976 | Cheskis et al. | 420/489 |
| 4,222,771 | 9/1980 | Oda et al. | 420/67 |

FOREIGN PATENT DOCUMENTS

| 1149922 | 6/1963 | Fed. Rep. of Germany | 73/838 |
| 0706741 | 12/1979 | U.S.S.R. | 73/840 |

OTHER PUBLICATIONS

Foxboro Bulletin, "Test Results are Automatically Recorded", Aug. 1964.

Primary Examiner—Stewart J. Levy
Assistant Examiner—Robert R. Raevis
Attorney, Agent, or Firm—Bruns and Wall

[57] ABSTRACT

A rupture testing procedure is carried out on metal foils at a number of process temperatures to evaluate their suitability for use in printed wire multilayer circuit boards. The test stand has a heated platen capable of heating foil test samples up to solder float temperatures (e.g. 550° F.) and an interchangeable cover with a circular aperture that is selected to match the foil thickness. Gas under pressure is admitted to the platen and the unsupported part of the sample bulges out until the sample ruptures. A plot is made of samples for temperature, burst pressure, and bulge height at burst, and the results are used to accurately classify or grade the foil. Creep rupture can also be tested at elevated temperatures to provide further foil quality information.

16 Claims, 4 Drawing Sheets

APPARATUS FOR RUPTURE TESTING METAL FILMS

BACKGROUND OF THE INVENTION

This invention relates to the testing of copper or other foils, and in particular the rupture testing of copper foil for laminates and plated through hole (PTH) deposits as used in printed wiring circuit boards.

Mullen testers of various sorts have frequently been employed for rupture testing the bursting strength of copper, aluminum or other foils and films. Various Mullen testers are described in the literature, and in this connection, reference is made to Smith U.S. Pat. No. 2,332,818, Oct. 26, 1943; Hollis U.S. Pat. No. 2,565,371, Aug. 21, 1951; Lovette U.S. Pat. No. 3,160,002, Dec. 8, 1964; and Schlegel U.S. Pat. No. 3,600,940, Aug. 24, 1971.

Mullen tester devices typically clamp a test sample of sheet material, which can be paper, cloth, fiberboard, metal foil, or synthetic material, between flat plates which have circular openings. Fluid under pressure forces a rubber diaphragm to expand through the apertures of these plates, and to exert a constantly increasing pressure against the unsupported area of the sheet material. This pressure is measured by a pressure gauge. When the bursting point of the sheet material sample is exceeded, the material tears, the pressure drops, and the pressure gauge indicates the burst pressure of the material.

Some of these testers also have a dial micrometer with an operating stem or probe which extends axially through the outer circular aperture against the sample. As the pressure is increased, the sample under stress will deform and dome until the burst or rupture point. The dial micrometer provides an indication of the material deformation under the various stressing pressures, and the maximum deformation corresponding to bursting or rupture.

Other rupture testers have also been proposed, e.g., in Getchell U.S. Pat. No. 2,525,345, Oct. 10, 1950; Biondi U.S. Pat. No. 3,736,794, June 5, 1973; Beckstrom U.S. Pat. No. 3,618,372, Nov. 9, 1971; Zacios U.S. Pat. No. 3,548,647, Dec. 22, 1970; and Tasker U.S. Pat. No. 2,748,596, June 5, 1956. These testers usually involve impacting an object onto the sheet or foil sample. The Tasker device carries out testing in a heated or refrigerated atmosphere.

There has recently arisen a need for improved testing techniques, particularly to establish performance requirements for copper cladding laminate foils and for PTH deposit quality in printed wire multilayer circuit boards (PWMLBs). Because of advances in integrated circuit technology and resultant miniaturization of components, quite sophisticated multilayer circuit boards have resulted. Because of the high cost and high performance requirements of these, the performance characteristics of the metal films employed as printed conductors or as plated through holes, should be known rather precisely.

The most recent impetus for performance improvement stems from the desirability for the surface mounting of components, from the electrical and thermal constraints imposed by high density component assembly, and by high speed circuit design. These advances make it imperative to construct PWMLBs with predictable and consistent properties in order to meet performance needs.

Of late, experience in using advanced, thermally stabilized multilayer substrates for high density assemblies shows that they are susceptible to premature failure due to the microcracking of the interconnecting conductive traces, including both the inner layer foil and the plated through hole (PTH). In some cases, fracture is initiated by a thermal stress, and the microcrack propagates during thermal cycling. In other cases, failure occurs by a tensile over-stress or by creep rupture. For either failure mechanism, the result is an open circuit condition and the loss of a completed, and usually expensive PWMLB.

Microcracking often occurs in the barrel of a PTH, at a PTH corner, or at the junction of the PTH with an interior layer. The fracture surfaces are typically quite brittle, and the studies of numerous failures has revealed little or no evidence of plastic deformation.

Fracture in a given PWMLB appears to be dependent on three factors: (1) a Z-direction thermal stress of sufficient magnitude to initiate fracture, (2) design- or process-induced stress risers, and (3) the presence of electrolytic copper with low hot strength. To date, most of the attention with regard to microcracking has been given the first two. Thus, there still remains a need to quantify the mechanical properties of copper conductors in PWMLBs with respect to strength and ductility at elevated temperatures. Since this information is obtained before the copper is used in a PWMLB, it can be used to prevent the use of a grade of electrolytic copper that is susceptible to premature thermal stress failure. In addition to eliminating failure under some conditions, this approach provides some latitude with regard to the handling of the other two factors that are mentioned as contributors to microcracking.

A printed wiring board (PWB) is the primary method now used in the electronics industry for the interconnection of circuits. A large share of the PWBs in use are produced by the fabrication of copper-clad laminates from which the copper is selectively removed by a photolithographic process to define a circuit interconnection pattern. Most of the copper used as conductor traces is supplied to laminators by a relatively small number of producers who make it in foil form by electrolytic deposition. The laminator then applies this foil to a dielectric substrate for subsequent sale to the PWB fabricator.

When the user of the laminates completes the fabrication of a multilayer printed wiring board, the circuit traces on each of the individual layers are interconnected by a plated-through-hole (PTH) process. Therefore, all of the conductors on a structure such as this are made of electrolytic copper, the surface and inner layers being done by an outside source, and the PTH deposition being done by an in-house plating operation.

It is possible to some extent to control the plating process and control contamination of the copper electroplate by means of a plating bath analysis. However, along with a capability for monitoring the condition of the plating solution, there is a need for determining and monitoring the elevated temperature mechanical properties of the resultant deposit. Control over these properties can provide control of the microcracking phenomenon.

A basic procedure for bulge testing samples of electrolytic foil has been described in T. A. Prater and H. J. Read, The Strength and Ductility of Electro-deposited Metals, Part I, Plating, Dec. 1949, and Part II, Plating, Aug. 1950. This procedure is also discussed in V. A. Lamb, C. E. Johnson, and D. R. Valentine, Physical and Mechanical Properties of Electrodeposited Copper, J. Electrochemical Soc., Oct. 1970. The Mullen rupture test of hydraulic bulge test as identified above, is widely used to determine the stress-strain properties of metal sheets and foils. However, the rubber diaphragm and hydraulic fluid used in conventional Mullen testers preclude their use with very thin sheets of electrodeposited foils. Also, current Mullen testers do not have a capability for testing at elevated temperatures.

OBJECTS AND SUMMARY OF THE INVENTION

It is an object of this invention to provide a rupture testing technique which is suitable for measuring the stress train properties of metal film under both mechanical and thermal stress conditions.

It is another object to provide testing apparatus for carrying out this rupture testing.

It is yet another object to provide testing apparatus that is easily used with metal foils or films of various thicknesses.

According to an aspect of the present invention, rupture testing is carried out as follows. A sample of the metal film, usually 10 cm square, is prepared and is placed on the platen of a test station. The platen has a heater for heating the sample to a desired test temperature that corresponds to a process temperature, i.e. from room temperature to the highest expected soldering temperature. For example, testing temperature should go at least to solder float temperature, 550 degrees F. (288 degrees C.). The sample is clamped against the platen by means of an apertured cover plate that has a circular aperture of a desired diameter. The apertured plate is mounted in a clamping plate that descends onto the platen, and the cover plate is interchangeable in the clamping plate so that for foils of lesser or greater thickness, an aperture plate can be used having an aperture of lesser or greater diameter.

The sample is heated to the desired temperature on the platen, and pressurized gas is fed through a central outlet in the platen to apply pressure against the metal film sample.

In a preferred mode, the pressure increases at a rate of one psi/sec while the sample is held at a constant test temperature. Measurements are made for bulge height at 10 psi intervals. The bulge height at rupture and the rupture pressure for each test temperature are recorded. Since this test yields data points for pressure, bulge height, and temperature, any combination of these variables can be used for an evaluation of material properties. However, for quality control purposes, a valid comparison between foil types is most easily obtained by a plot of rupture pressure versus test temperature. From these data, a measure of mechanical strength and ductility can be obtained.

When a pressure is applied to the foil, the foil deforms under balanced biaxial tension, and this deformation continues until fracture occurs. From the measured values for rupture pressure and bulge height, from the geometry of an axisymmetrical bulge, and from membrane stress and strain relationships for thin walled pressure vessels, we can obtain values for comparison with values obtained from a uniaxial tensile test from the following relation:

$$R = (r^2 + h^2)/2h \qquad [1]$$

where R is the radius of curvature of the bulge, r is the radius of the aperture, and h is the height of the bulge. Then, we can obtain tensile strength from the relation:

$$TS = PR/2t \qquad [2]$$

where TS is the nominal tensile strength, P is the rupture pressure, R is the radius of curvature and t is the original thickness. These mathematical relationships can be more fully developed for obtaining true stress, true strain, nominal strain, ductility, and elongation values from bulge rupture tests, by taking into account the basic differences between the tensile test and the rupture test. However, this degree of detail is probably not necessary for effective use of the rupture test for quality control purposes.

Creep-Rupture Test

This procedure differs from the dynamic approach only in that a pre-set, constant pressure is applied and an up-counting timer is used for measurement of the delayed-fracture time at constant pressure. Otherwise, the test equipment is identical. In either case, the assembly is designed such that tests can be made at any temperature between room temperature and 550 degrees fahrenheit, and at any pressure up to 80 psig. To allow the testing to be done on the same pressure scale, this cover plate aperture is variable for accommodating half-ounce or one-ounce foils.

Creep-rupture properties are obtained by the application of a constant pressure at constant temperature. Measurement is made for the time-to-rupture at each test pressure, and a plot of rupture pressure versus time at any test temperature will distinguish between the different types of copper. Typically, the nearer to the rupture pressure that the test pressure is set, and the higher the test temperature, the shorter is the time to fracture. Also, there is a distinctive difference in the delayed fracture characteristics of the various types and classes of foil and this allows their segregation according to rupture quality.

Mechanical Testing of Foil

For the testing of half-ounce and one-ounce copper foil, sample pieces are cut into 4 inch×4 inch (10 cm×10 cm) squares. Nine test pieces are needed per lot, with three being used at each of three test temperatures (Room temperature or 70 degrees F., 350 degrees F., and 550 degrees F.) for a measure of dynamic rupture properties. For determining delayed-fracture characteristics, at least six test pieces are needed per lot, with three being used at each of two test pressures (e.g., 50% and 75% of the dynamic rupture pressure) and one test temperature (350 degrees F.). As is true of the dynamic version, this test can be conducted over a much broader set of pressure, temperature, or time test conditions if so desired.

From its flat initial condition, the resultant test piece takes on a hemispherical shape due to the applied pressure. The radius of curvature and the height of the bulge will vary, of course, from sample to sample. However, the bulge radius of curvature will depend on tensile strength TS and thickness t of the metal foil sample test piece.

The charts of burst pressure versus temperature and of burst temperature versus bulge height can be plotted to show graphically the characteristics and dependability of the metal foil material.

The testing device and method of employing same are illustrated herebelow with reference to a single preferred embodiment, which is given as an example.

DETAILED DESCRIPTION OF THE PREFERRED EMBODIMENT

Figure 1:
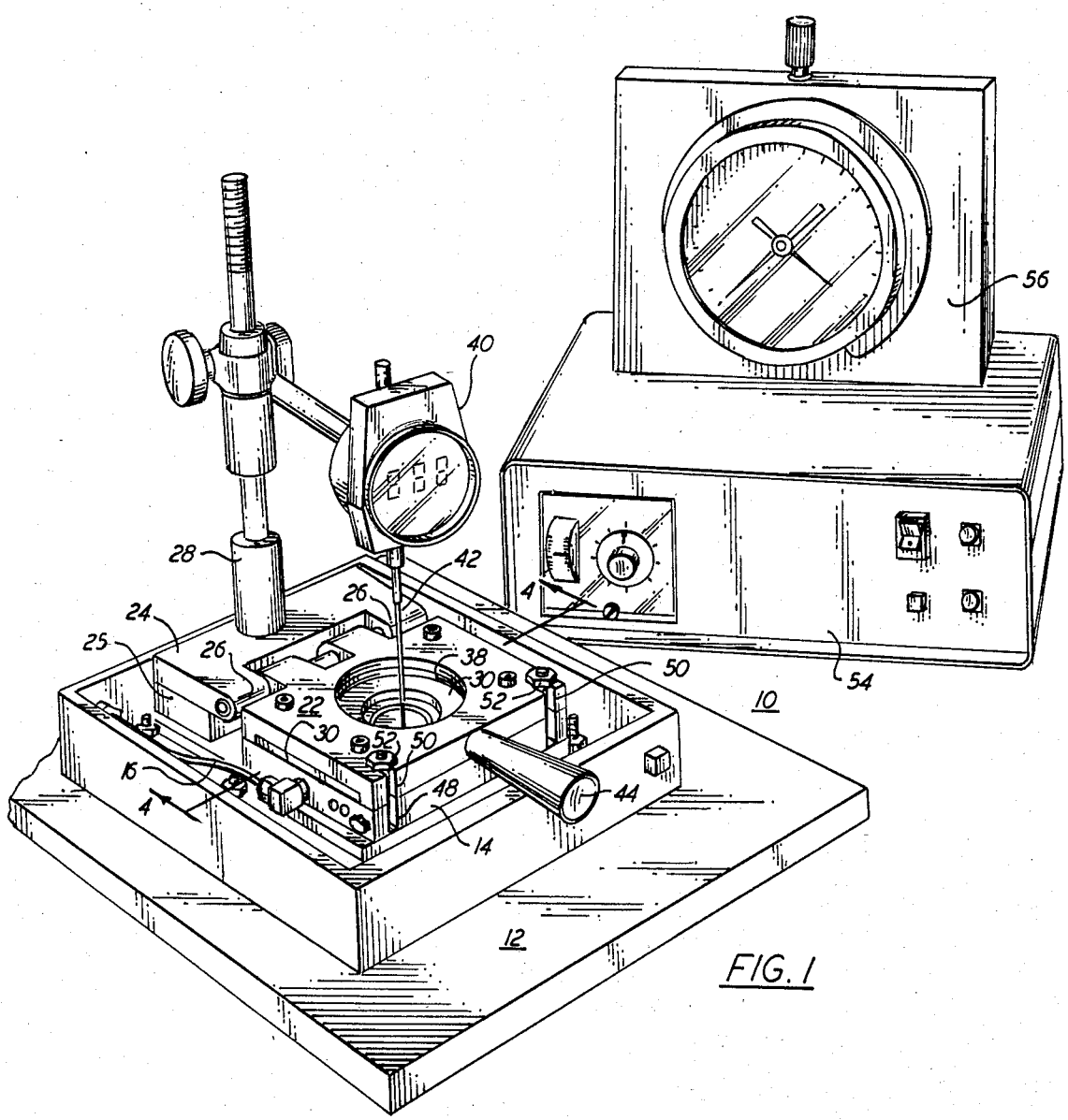
FIG. 1 is a perspective view of testing apparatus according to an embodiment of this invention.
Figure 2:
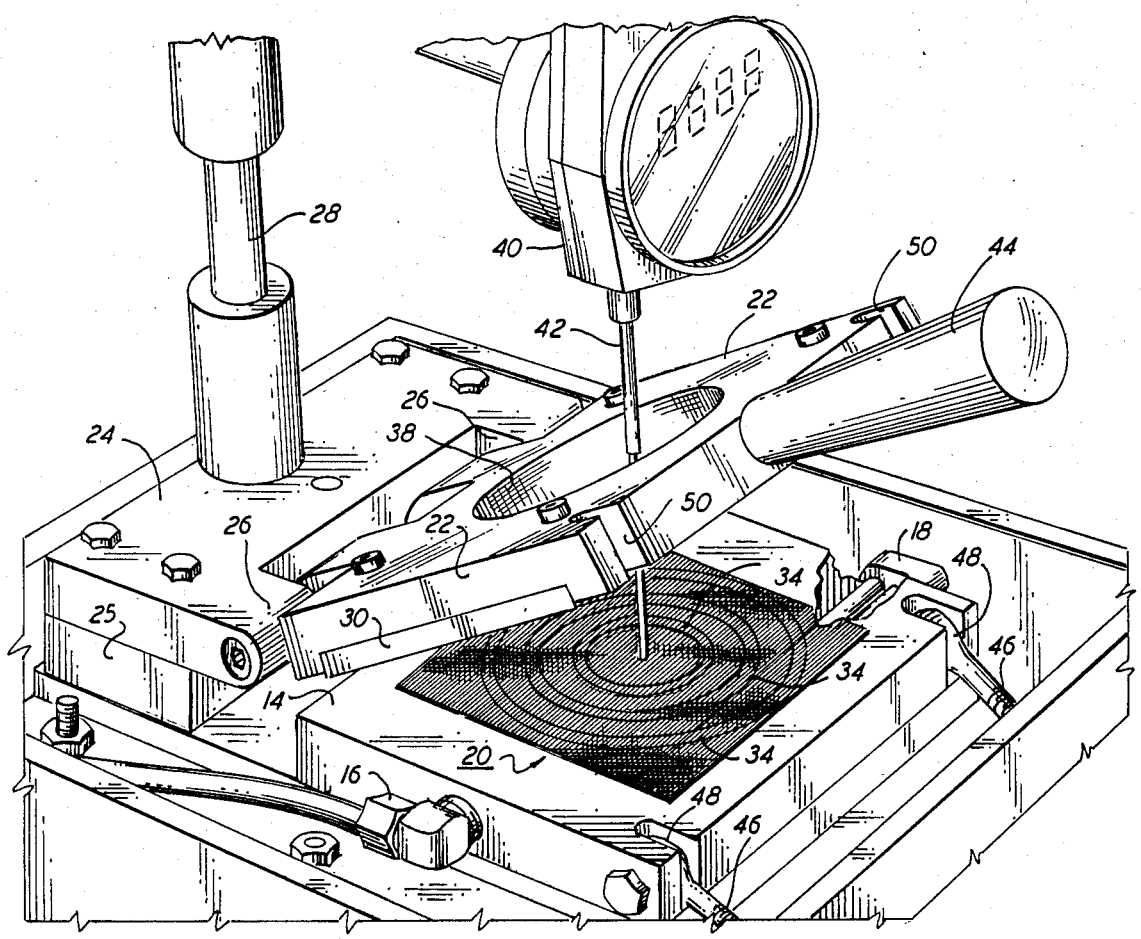
FIG. 2 is a second perspective view showing the device in condition for loading or removing a sample test piece.

With reference to the Drawing and initially to FIGS. 1 and 2, burst testing apparatus 10 according to one embodiment of this invention has a test stand or base 12 carrying a platen 14. The platen is of the heated type and has a generally flat upper surface. An air inlet 16 carries pressurized air or another gas such as N to an opening 17 at the center of the platen upper surface. Other gases (argon, helium, etc.) could be used, or the apparatus adapted for a silicone hydraulic fluid. A pair of cartridge type electric heater elements 18 are also situated in the platen 14. These elements 18 are perhaps better shown in FIGS. 4 and 5. These are capable of delivering temperatures up to about 800 F.

Sample test pieces are cut as 4-inch by 4-inch (10 cm × 10 cm) squares of the metal sheet or foil material. One such sample piece 20 is shown lain upon the upper surface of the platen 14.

A hinged cover seal plate or clamping plate 22, shown in a lowered or clamping position in FIG. 1 and in a raised or open position in FIG. 2, is pivotally mounted on a hinge block 24 that is affixed to a spacer bar 25 on the test stand 12 relative to the platen 14, and a pin-type hinge 26 connects the clamping plate 22 and the block 24. A height-gauge post or rod rises from the block 24 and mounts a linear displacement device to be described later.

On the side of the clamping plate 22 that is disposed against the sample test piece 20 is an interchangeable aperture plate or cover 30. This aperture plate 30 has a central circular opening 32 whose diameter (i.e. 2r) is known, and is selected to optimize the relation [1] above for the thickness of the sample 20. Generally, two of these plates 30 are required, one for one-ounce foil and the other for half-ounce foil. However, foils from 0.0001 to 0.003 inches can be accommodated. The plate 30 is removably affixed, i.e., by set screws, to the plate 24.

An annular reinforced PTFE (Teflon) sealing ring 34 surrounds the air inlet opening 17, and the cover or aperture plate 30 biases the sample piece 20 against the sealing ring 34 to effect a pressure seal against the platen 14. The sealing ring 34 is favorably seated in an annular channel 36 formed in the top surface of the platen 14. Also, there are preferably a number of these sealing rings 34 of various diameters seated in respective concentric channels 36. In other words, an assortment of the sealing rings 34 are provided corresponding to a number of possible diameters of openings 32.

A large circular cavity 38 is provided in the cover seal clamping plate 22 generally in registry with the circular opening 32 of the aperture plate 30. The cavity 38 is not through the clamping 22 when a noise muffler (not shown) is attached. The aligned cavity 38 and opening 32 admit access to the surface of an unsupported exposed disc of the sample 20.

A linear displacement transducer, here embodied as a dial micrometer 40, is mounted on the post 28 and has a probe or arm 42 extending down through the openings 38 and 32 to contact the sample 20. A swing assembly (not shown) permits the micrometer 40 to be moved when the cover seal plate 22 is opened. This instrument measures the vertical distortion of the sample 20 during the test, and gives the value of bulge height h in equation [1]. From this, tensile strength TS can be derived as in equation [2].

The clamping plate 22 has a handle 44 on the side opposite the hinge 26, and also has hold down arrangement including a pair of swing bolts 46 mounted in recesses 48 in the platen, corresponding cutouts 50 which align with the recesses 48 when the clamping plate 22 is lowered to the platen 14, and threaded fasteners 52 (here, nuts). A torque wrench can be used to turn the nuts 52 down on the bolts 48 so that the same amount of holddown force is applied for each sample in a given test series. However, other hold down means could be employed here to advantage; for example, over-the-center clamps could be substituted for the bolts 44 and nuts 52.

As further shown in FIG. 1, a heater controller 54 is coupled to the heater elements 18 and a pressure controller 56 with an analog dial pressure indicator 58 and an incorporated rupture sensor 60 is coupled to the air inlet 16 of the platen 14. The controller 56 has a pressure on/off indicator lamp and switch, pressure regulator and flow control, and a lazy-hand peak indicator incorporated with the pressure indicator 58. The heater controller 54 has a power gauge and a temperature indicator/controller. Pressure, height, temperature, and time indicators could be digital, with or without computer compatibility, as desired.

Figure 3:
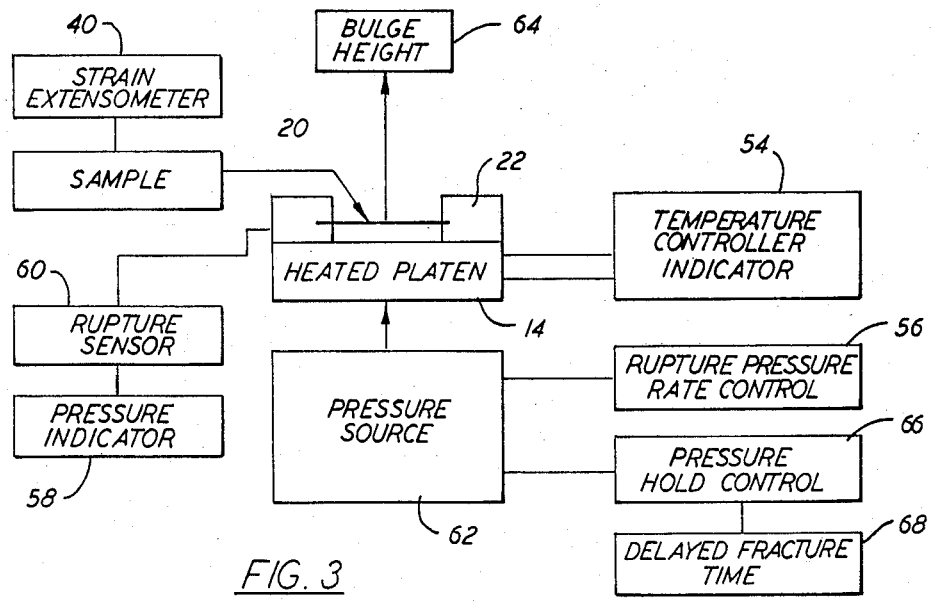
FIG. 3 is a block diagram for explaining the test procedure of this invention.

As illustrated schematically in FIG. 3, when the sample 20 is clamped by the clamp plate 22 against the heated platen 14, pressurized gas or air is supplied from a source 62 and is controlled by the pressure controller 56. Pressure is increased gradually (e.g. at a rate of 1 psi per second), until a rupture of the sample 20 is sensed by the pressure sensor 60. The bulging of the unsupported part of the sample 20 is measured by the displacement transducer 40, and produces a bulge height reading 64. The transducer or micrometer 40 here is a digital instrument, with an automatic peak hold capability and which can automatically forward the burst point bulge height data to automatic data processing equipment.

A pressure-hold controller 66 is connected with the pressure source 62 to carry out delayed rupture testing, and a delayed fracture timer 68 is coupled to the controller 66.

Figure 4:
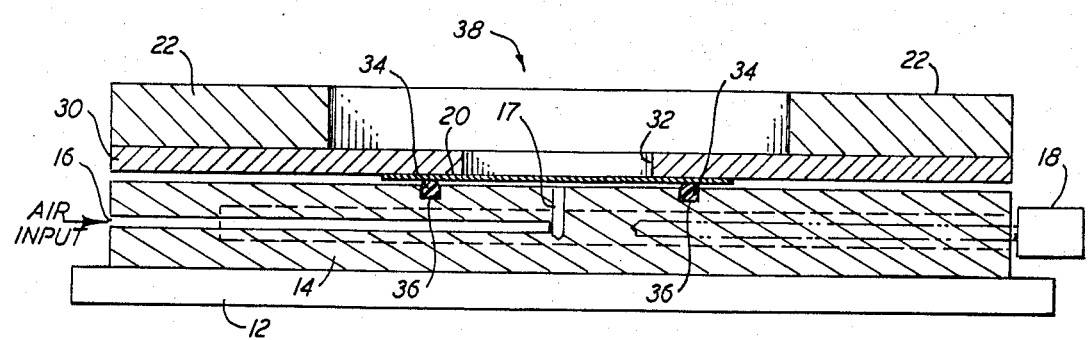
FIG. 4 is a section view of the test device of this invention taken at line IV—IV of FIG. 1.
Figure 5:
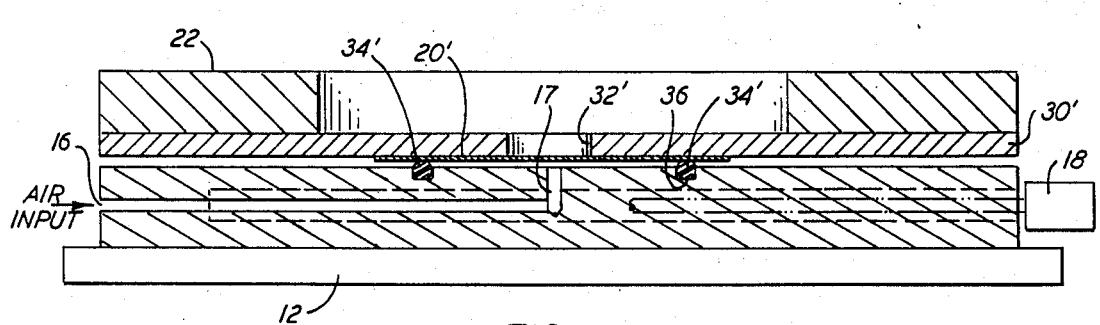
FIG. 5 is a section view similar to FIG. 4 showing the device but with an alternative aperture plate.

As shown in FIG. 4, when a test is conducted on one-ounce foil sample 20 (i.e., copper foil one mil thick) the aperture plate or cover 30 with the standard aperture 32 is employed. However, as shown in FIG. 5, if the test is carried out on a half-ounce foil 20' (i.e., foil 0.5 mils thick), an alternate aperture plate 30' having an aperture 32' is interchanged with the plate 30. The aperture 32' is about one-half the diameter of the circular aperture 32, so that the occurrence of rupture will be on the same order for both foils for the same range of pressure.

Although not shown here, an exhaust silencer covers the circular opening 38 and, preferably, a cover overfits the platen 14 and plate 24 of the test stand 12, to reduce to within OSHA-acceptable levels the loud burst or pop that occurs when the pressure-distorted foil sample 20 gives way.

Tests have been carried out employing the method and apparatus of this invention generally as described hereinabove. By these tests, quality control standards are established for a number of roll-type foils and for electrodeposited foils.

Numerous dynamic rupture tests were made on half-ounce (0.0007") and one-ounce (0.0014") Type E (electrolytic) and Type W (wrought or rolled) copper foils. Commercial material representing foil production from the major foil suppliers was used to establish plots of rupture pressure versus test temperature for each type of foil at the two thickness levels. In an iterative process, the initial plots were used to classify larger numbers of foil and these results were then used further to refine the standards. Following this procedure, standard plots were developed, and now exist for Type E, Class 1; Type E, Class 3; and Type W, Class 7 foils. (As defined by industry standard IPC-CF-150).

Figure 6:
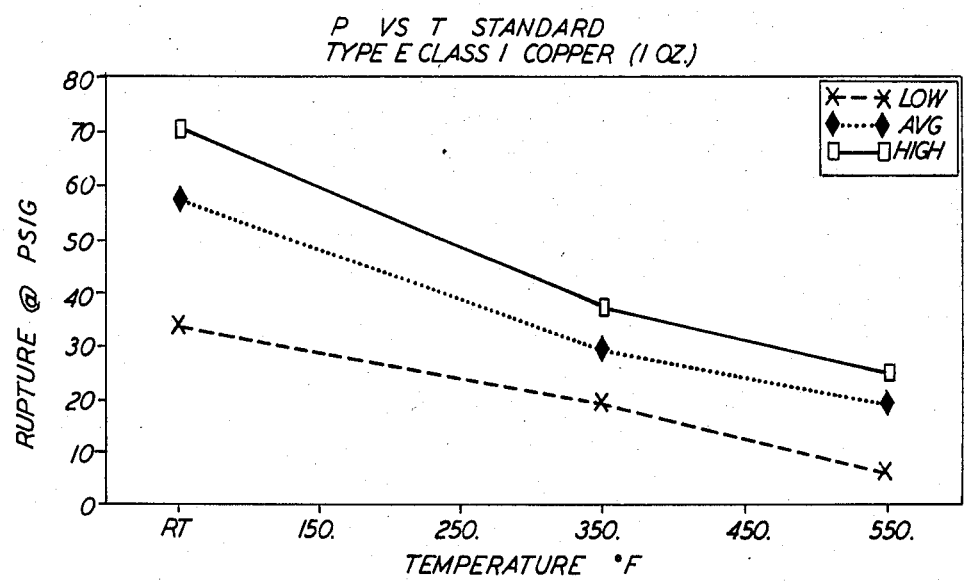
FIGS. 6, 7, 8, 9 and 10 are charts of test results indicating performance characteristics of various electrolytic and rolled copper films.

FIG. 6 shows the effect of test temperature on the rupture pressure of one-ounce Type E, Class 1 copper foil. Under these test conditions, the average rupture pressure at the solder-float temperature (550 degrees F.) is about 40% of that at room temperature. Of even more concern are the lowest rupture values, which have ranged down to 6 psig when the foil is stressed at the highest test temperature. This set of curves then represents copper foil that is of Type E, Class 1 quality.

Figure 7:
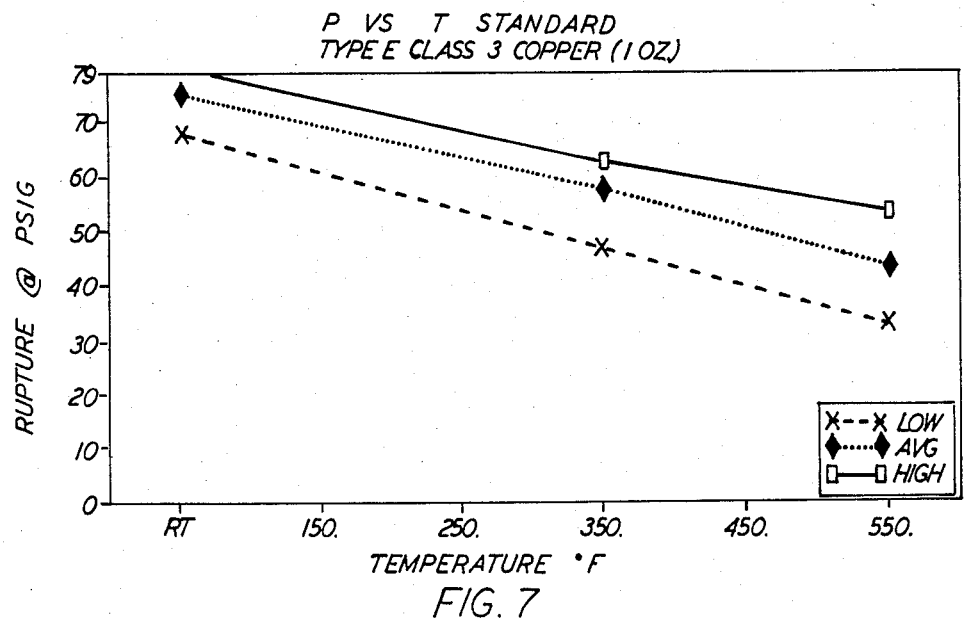
Figure 8:
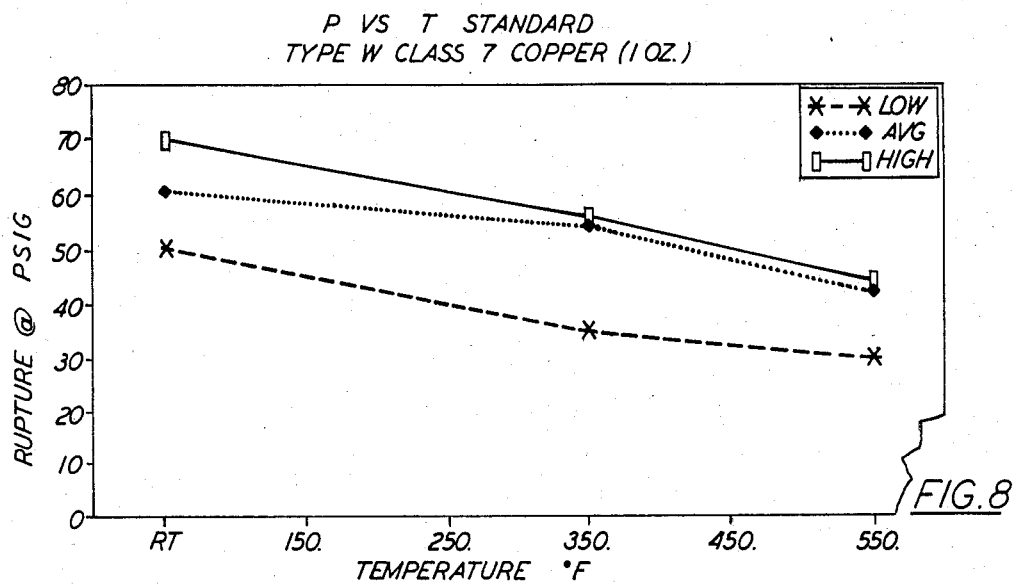

FIG. 7 shows the effect of test temperature on the rupture pressure of one-ounce Type E, Class 3 copper foil, and FIG. 8 shows the results for Type W, Class 7 foil. These results show that the average rupture pressure at 550 degrees F. is over 60% of that at room temperature for these foils. Better yet, they maintain rupture strengths of over 35 psig at solder float temperatures, a significant improvement over Class 1 foil. The other observation worth mentioning is that the Class 1 foil burst properties overlap into the Class 3 and Class 7 property range at room temperature, so the elevated temperature tests will provide a more positive indication of the correct foil classification. In other words, room temperature testing is probably not sufficient for proper foil characterization.

Foil Characterization

Other than by variations in material characteristics, rupture test results are influenced most by strain rate, by creep and by sample thickness.

The standards that have been established for these foils can now be used for the classification of foils from new lots of material, and this grading can be done before the new foil is laminated or used in PWMLB fabrication. Rupture strength for one-ounce foil that was obtained from commercial suppliers of electrolytic and rolled copper foil has been compared with the previous categorizations. As expected, when the different types and classes of foils are categorized by their comparison against the set of standard plots, each falls into the classifications which had been developed earlier.

PTH Copper Characterization

As a part of the classification process, foil samples from in-house plated through-hole (PTH) operations at several PWMLB facilities were made and tested. These samples represented copper deposits from the common plating solutions, including sulfate, pyrophosphate and cyanide. When used in conjunction with the standards for the commercial foils, the PTH copper can be graded as being the equivalent of either the Class 1 or the Class 3 foil. In this way, PTH samples can be used to monitor the condition of the PWMLB plating process, i.e., through a determination of the mechanical properties at different times during the life of the plating bath.

Unlike the commercial foil samples, for the testing of PTH copper, deposits must be obtained directly from the plating solution. Foil samples plated out of the plating bath can be used for determining the PTH equivalent of foil properties. This permits the use of the same standards for PTH deposits as for commercial foils.

Type E foil test pieces, a polished stainless steel panel is loaded in a rack in preparation for copper plating. The panel passes through the plating line where it is coated with either half-ounce or one-ounce copper. The plated copper is taken off the panel for testing. Once in foil form, the sample sheet can be sheared into 4×4 inch test pieces, to be tested for rupture strength in the same way that was previously described for commercial foils. In other words, the electroplated copper foil deposited on the stainless steel panel or plate is stripped from the panel to produce samples for testing. These samples are tested and the testing provides an indication of the quality of the plating bath.

Although plating conditions for a large, flat panel are not exactly like those in the local region of a PTH, the resultant deposit should be somewhat representative of the copper that would be deposited on a PWMLB. At the very least, foil made in this way provides a means for tracking the condition of a plating bath through the use of mechanical tests on the deposit, an approach that is commonly used for making tensile tests on plated deposits.

In this manner, test pieces have been made from a PWMLB production plating line that uses acid copper sulfate plating chemicals. The initial bath make-up, with regard to composition, additives, etc. was prepared according to the supplier's recommendations. A series of PTH foils were taken from this plating operation over a period of eight months, and the foil was tested for rupture properties by using the procedure described earlier.

Figure 9:
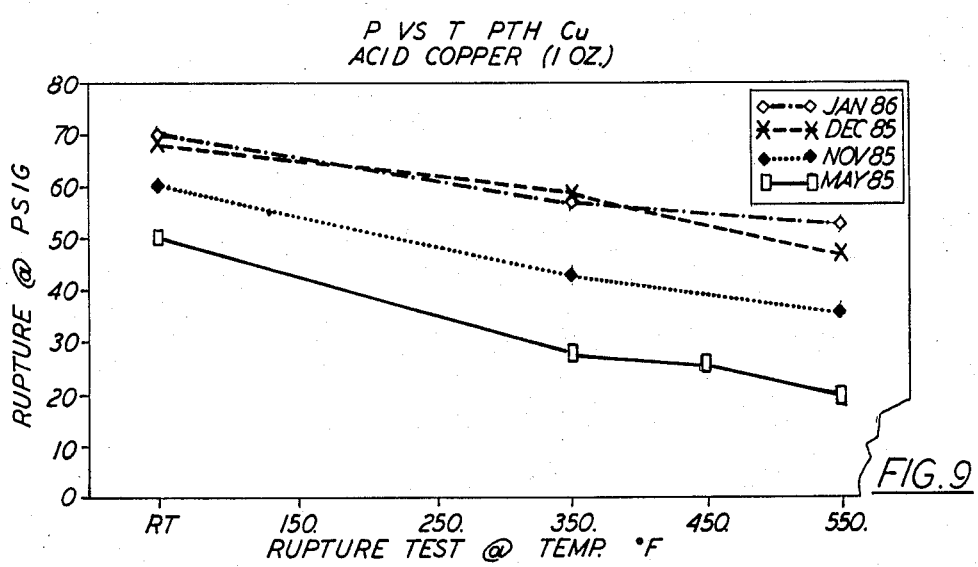

The results of these tests for PTH electrodeposited foils is shown in FIG. 9.

The simplest way to examine and to interpret these data is to overlay onto this set of curves the standard plots for Class 1 and Class 3, foil (i.e., FIGS. 6 and 7). When this is done, it can be seen that the May 1985 PTH foil is in the average Class 1 category. The Nov. 1985 PTH foil is just above Class 1 and into the lower level of the Class 3 quality range. The December 1985 and the January 1986 PTH foil materials are both well into the Class 3 quality range.

The plating bath represented by these foil samples is an acid copper sulfate solution. As mentioned, the bath had been set up in May 1985, to the supplier's recommendations. The PWMLB product from this plating line at that time exhibited PTH corner cracks is 50% of the boards. By November 1985, the plating bath was operating with modified quantities of additives, especially organic brighteners. This change is reflected in the improved rupture properties of the test pieces as well as in the total elimination of PTH corner cracks.

Quality Control by Creep-Rupture Testing

Figure 10:
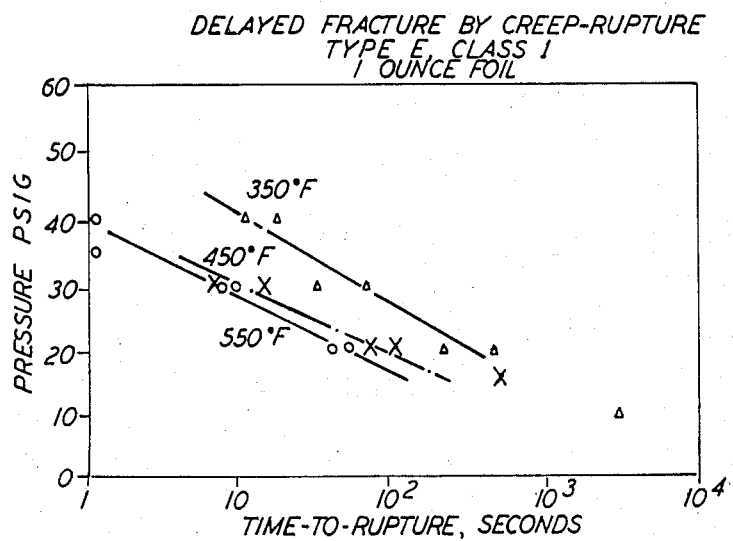

When a foil test piece is held at constant pressure and constant temperature, rupture occurs due to creep. A measure of time-to-fracture provides an indication of the creep-rupture resistance of the material under test, and this characteristic varies according to the type of foil that is being tested. Using the static pressure test method, an evaluation was made of fifteen lots of half-ounce commercial foil. Shown in FIG. 10 are the results as compiled for ten lots of Type E, Class 1 foil.

These results show that the time-to-rupture increases with decreasing pressure and that the creep-rupture pressure decreases with increasing temperature. More importantly, for Class 1 foil, rupture will occur in less than 10 seconds at pressure levels of from 12 to 25 psig when the foil is stressed at temperatures above 350 F. This implies that Type E, Class 1 inner layer or PTH interconnections could be damaged during solder-float testing where the requirement is for a 10 second exposure at 550 F. Also, thermal cycling, soldering or solder repair could cause fracture with some very moderate Z-direction stresses.

Static rupture tests were made on material from five lots of half-ounce Type E, Class 3 foil. The same trends present with the Class 1 material were noted with the Class 3 foil. An important difference is that the Class 3 foil has much better creep-rupture strength at any test temperature, i.e., relatively high pressures are needed in order to cause fracture in times under ten seconds. This difference in delayed-fracture characteristics distinguishes between the quality of the two classes of foil through the use of the static rupture test method.

Another phenomenon which is peculiar to Type E, Class 3 material, is evident upon examination of the 550 F. test results. Since early creep-rupture does not occur, the foil is annealed during the test cycle. This improves the rupture properties of the foil, as would an anneal before the rupture test. This does not happen with Class 1 foil during the 550 F. test.

PWMLB structures for high-speed, high-density circuits are prone to failure due to the microcracking of electrolytic copper interconnections. The failure can occur in the foil that makes up the inner layer traces or in the PTH deposit that forms the layer-to-layer interconnections. Because of the high value of the PWMLBs, it is imperative that the distinctive differences in the quality of Type E copper foils be detected before its use in a PWMLB. In particular, the strength of some Type E copper can be very low when the material is hot, and the use of this poor quality material in a PWMLB results in PTH and inner-layer microcracking.

Since the PWMLB failures in question are induced by a thermal stress, and since the poorer grades of Type E materials used in these structures are susceptible to premature failure under thermal stress, the use of elevated temperature rupture and creep-rupture testing provide an excellent means for screening copper foil (or its PTH equivalent) in order to eliminate the problem of Type E copper microcracking in advanced PWMLBs.

Of course, the testing method and the apparatus for carrying it out are not limited only to the specific embodiment that has been set out above as an example. For example, an automated feed system could be employed for testing the foils, and the testing could be carried out under robotic control. Also, the testing is certainly not limited only to copper foils, but is intended also for nickel foils, and could be applied to foils of other materials, or to laminates. The test data can be collected and plotted automatically in a micro- or mini-computer. The testing can be carried out also at cold and extreme cold temperatures (e.g. 32 F. to −55 F.). In other words, it should be recognized that the invention is not limited precisely to the above embodiment. Rather, many modifications and variations thereof would present themselves to those skilled in the art without departing from the scope and spirit of the invention, as defined in the appended claims.

What is claimed is:

1. Apparatus for hot rupture testing a metal foil of electrolytic or rolled copper of the type used in the fabrication of printed wiring multi-layer boards, the apparatus comprising a heated platen having an upper surface of dimensions to accommodate a square, flat sample of said metal foil and including ring grooves for the acceptance of high temperature ring seals, heater means therein for rapid heating of the sample on said platen to controlled temperatures in the range of from room temperature through soldering temperatures of substantially 288° C., with a temperature control sensor located near the platen surface, and a fluid passage for subjecting said sample to fluid pressure;

cover plate with clamping means for pressure tight sealing of said sample against said platen, and including an interchangeable aperture plate removably carried on said cover plate and which is urged against said sample, the aperture plate having a circular aperture therethrough;

sealing means formed of a high temperature sealing ring in one of said ring grooves for forming and maintaining a seal between said sample and said platen when said cover plate bears against said sample; and means for sensing peak height and peak pressure applied to said sample.

2. Rupture testing apparatus as in claim 1 further comprising at least one other aperture plate interchangeable with the first mentioned aperture plate, and having a circular aperture of a size different from that of the first mentioned circular aperture.

3. Rupture testing apparatus as in claim 2 wherein said cover plate has recesses for slidably receiving said one and said other interchangeable aperture plates.

4. Rupture testing apparatus as in claim 2, comprising an assortment of circular ring seals dimensioned to correspond to the apertures of said aperture plates.

5. Rupture testing apparatus as in claim 1 in which said cover plate includes a mount fixed relative to said platen and on which said cover plate is hingedly mounted for closing against the sample on said platen, and hold down means for releasably securing said cover plate against said platen with said sample sandwiched therebetween.

6. Rupture testing apparatus as in claim 5 wherein said cover plate has a centered guide hole therethrough in registry with the aperture in said aperture plate.

7. Rupture testing apparatus as in claim 6 further comprising linear displacement measurement means including a probe passing through said cover plate guide hole and said aperture plate circular opening to contact said sample, for measuring bulge height in said sample induced by the fluid pressure applied to said sample, including automatic peak-hold means for automatically retaining the measured bulge height at burst.

8. Method of hot rupture testing a metal foil of the type employed as a conductive layer or interconnecting plated through hole in a printed wiring multilayer board, the foil being a thickness on the order of 0.0001 to 0.0030 inches, comprising the steps of:
- placing a sample of the foil, of a thickness between 0.0001 and 0.0030 inches, on a platen that has an associated heater and an opening for admitting a fluid under pressure against said sample;
- clamping the sample against said platen with an aperture plate that has a circular aperture of a predetermined diameter selected in accordance with the thickness of the metal foil sample;
- heating said sample to a predetermined elevated testing temperature in the range above room temperature up to soldering temperature on the order of 288 degrees C.;
- applying fluid under controlled pressure through the platen opening against said sample to stress the sample to a burst point at which the sample ruptures; and
- measuring the fluid pressure at least at the sample burst point.

9. The method of claim 8 further comprising sealing said sample to said platen with an annular sealing member surrounding said opening.

10. The method of claim 8, further comprising the step of measuring the bulging of said sample through said circular aperture at least at said burst point.

11. The method of claim 10, further comprising testing samples of different thicknesses of said metal; and replacing said aperture plate with at least one other aperture plate of different aperture diameter when changing the thickness dimension of the tested samples.

12. The method of claim 11 in which said other aperture plate aperture diameter is smaller or larger in proportion to a reduction or increase in thickness of said samples, respectively, such that the burst point bulge measurement and burst point pressure measurement will be on the same order for the samples of differing thicknesses.

13. The method of claim 8 further comprising the forming of samples of said metal foil by suitably preparing a plate, passing said plate through an electroplating bath to deposit said metal film upon said plate, and stripping the metal foil from said plate to produce the samples for testing, so that the testing method provides an indication of the quality of the plating bath.

14. The method of claim 8 further comprising the hot rupture testing a metal foil of the type employed as an inner layer in a printed wiring multi-layer board, comprising the steps of placing a sample of the foil on a platen that has an associated heater and an opening for admitting a fluid under pressure against said sample; clamping the sample against said platen with an apertured plate that has a circular aperture of a predetermined diameter; heating said sample to a predetermined test temperature on the order of 288° C. corresponding to soldering conditions; and applying a fluid at a controlled predetermined rate.

15. The method of claim 8 further comprising similarly testing at least two further samples of said metal film but in which said heating is carried out for one of the further samples at room temperature and for the other of the further samples at an intermediate elevated temperature substantially midway between room temperature and said predetermined testing temperature.

16. Method of creep-rupture testing a metal foil of the type used as a conductive layer or interconnect in a printed wiring multilayer board, comprising the steps of placing a sample of the foil on a platen that has an associated heater and an opening for admitting a fluid under pressure against the sample, the foil sample having a thickness of about 0.0001 to 0.0030 inches; clamping the sample against said platen with an aperture plate that has a circular aperture of a predetermined diameter selected in accordance with the thickness of the metal foil sample heating said sample to a predetermined testing temperature corresponding to soldering temperature conditions one the order of 288 degrees C., applying fluid at a pressure equivalent to a fraction of the stress-rupture strength; holding said pressure until the stressed sample ruptures; and measuring the time that said predetermined constant pressure is applied until said sample ruptures.

* * * * *